(12) United States Patent
Kirchnavy

(10) Patent No.: US 10,508,976 B1
(45) Date of Patent: Dec. 17, 2019

(54) GAS SAMPLING DEVICE AND METHOD

(71) Applicant: Advanced Micro Instruments, Inc., Huntington Beach, CA (US)

(72) Inventor: Steven Kirchnavy, Orange County, CA (US)

(73) Assignee: ADVANCED MICRO INSTRUMENTS, INC., Costa Mesa, CA (US)

( * ) Notice: Subject to any disclaimer, the term of this patent is extended or adjusted under 35 U.S.C. 154(b) by 0 days.

(21) Appl. No.: 15/782,697

(22) Filed: Oct. 12, 2017

Related U.S. Application Data

(60) Provisional application No. 62/480,499, filed on Apr. 2, 2017, provisional application No. 62/480,322, filed on Mar. 31, 2017.

(51) Int. Cl.
| | | |
|---|---|---|
| *G01N 1/22* | (2006.01) | |
| *G01N 21/59* | (2006.01) | |
| *G01N 21/15* | (2006.01) | |

(52) U.S. Cl.
CPC ........... *G01N 1/2205* (2013.01); *G01N 21/15* (2013.01); *G01N 21/59* (2013.01)

(58) Field of Classification Search
CPC ...... G01N 1/2205; G01N 21/15; G01N 21/59; G01N 21/05; G01N 2021/151; G01N 21/3504; G01N 21/0303; G01N 2030/025; G01N 30/88; G01N 2001/2238; B01L 3/5027; B01L 3/502715; B01L 2200/0684;
(Continued)

(56) References Cited

U.S. PATENT DOCUMENTS

| | | | | |
|---|---|---|---|---|
| 2,930,237 A | * | 3/1960 | Fowle, Jr. ................ | G01N 1/26 55/459.1 |
| 4,462,238 A | * | 7/1984 | Goodfellow ............ | C21D 7/10 72/352 |

(Continued)

FOREIGN PATENT DOCUMENTS

WO    WO-9811432 A1 *   3/1998   ............. G01N 30/30

OTHER PUBLICATIONS

Kirchnavy, U.S. Appl. No. 62/480,322, filed Mar. 31, 2017.
(Continued)

*Primary Examiner* — Mohamed K Amara
(74) *Attorney, Agent, or Firm* — One LLP; Deepali A. Brahmbhatt; Joseph K. Liu

(57) ABSTRACT

A sampling device for a gas comprises a block member that includes a gas passageway that defines a flow path for the gas through the block member that has a length less than 36 inches. A liquid collection chamber within the block member along the flow path has therein a deflection plate that directs any liquid in the gas onto a surface of the plate downward into a lower sink zone of the chamber. The chamber includes a porous membrane along the flow path that acts as a barrier to liquid, allowing gas to flow through the membrane and into a passageway segment downstream of the membrane. A pair of mirrors at opposed ends of a light collection block are shaped to reflect multiple passes of light between the mirrors. At one end of the light collection block is a lens that focuses light on the mirror at the other end of the light collection block. A light detector near one end of the light collection block collects light after multiple reflections of the light off the mirrors.

5 Claims, 13 Drawing Sheets

(58) Field of Classification Search
CPC ......... B01L 3/502738; B01L 2400/082; Y10T 137/3724; G01M 3/205
See application file for complete search history.

(56) References Cited

U.S. PATENT DOCUMENTS

| | | | | | |
|---|---|---|---|---|---|
| 4,813,268 | A | * | 3/1989 | Helvey | G01M 3/205 73/40.7 |
| 4,970,904 | A | * | 11/1990 | Knotts | B60C 29/06 137/231 |
| 5,621,213 | A | * | 4/1997 | Barshad | G01N 21/33 250/252.1 |
| 5,720,650 | A | * | 2/1998 | Mauze | G01N 21/15 451/39 |
| 6,290,738 | B1 | * | 9/2001 | Holm | B01D 45/08 55/309 |
| 7,101,509 | B2 | * | 9/2006 | Chang | B01L 3/502 422/417 |
| 7,500,479 | B2 | * | 3/2009 | Nichols | A61M 15/00 128/200.21 |
| 8,613,233 | B2 | * | 12/2013 | Scott | G01N 1/2214 73/863.21 |
| 9,273,308 | B2 | * | 3/2016 | Link | B01F 3/0807 |
| 9,316,623 | B2 | * | 4/2016 | Seo | G01N 30/00 |
| 9,446,406 | B2 | * | 9/2016 | Gordon | B01L 3/5029 |
| 10,324,030 | B2 | * | 6/2019 | Sanroma | G01N 33/225 |
| 2006/0076482 | A1 | * | 4/2006 | Hobbs | H01J 49/009 250/287 |
| 2006/0144126 | A1 | * | 7/2006 | O'Brien | G01N 1/2202 73/23.42 |
| 2008/0051674 | A1 | * | 2/2008 | Davenport | A61B 5/087 600/561 |
| 2008/0121017 | A1 | * | 5/2008 | Shah | G01N 30/88 73/23.42 |
| 2010/0267092 | A1 | * | 10/2010 | Zenhausern | G01N 21/645 435/91.2 |
| 2011/0201099 | A1 | * | 8/2011 | Anderson | G01N 21/05 435/287.2 |
| 2011/0203583 | A1 | * | 8/2011 | Cozean | A61K 31/10 128/203.12 |
| 2013/0280132 | A1 | * | 10/2013 | Maskrot | G01N 21/05 422/83 |
| 2014/0202234 | A1 | * | 7/2014 | Burgon | G01N 21/15 73/31.07 |
| 2016/0348561 | A1 | * | 12/2016 | Higashi | F01N 3/021 |
| 2019/0154550 | A1 | * | 5/2019 | Wu | G01N 33/54306 |

OTHER PUBLICATIONS

Kirchnavy, U.S. Appl. No. 15/835,903, filed Dec. 8, 2017.
U.S. Appl. No. 62/480,322, filed Mar. 31, 2017 Steven Kirchnavy.
U.S. Appl. No. 15/835,903, filed Dec. 8, 2017 Steven Kirchnavy.

* cited by examiner

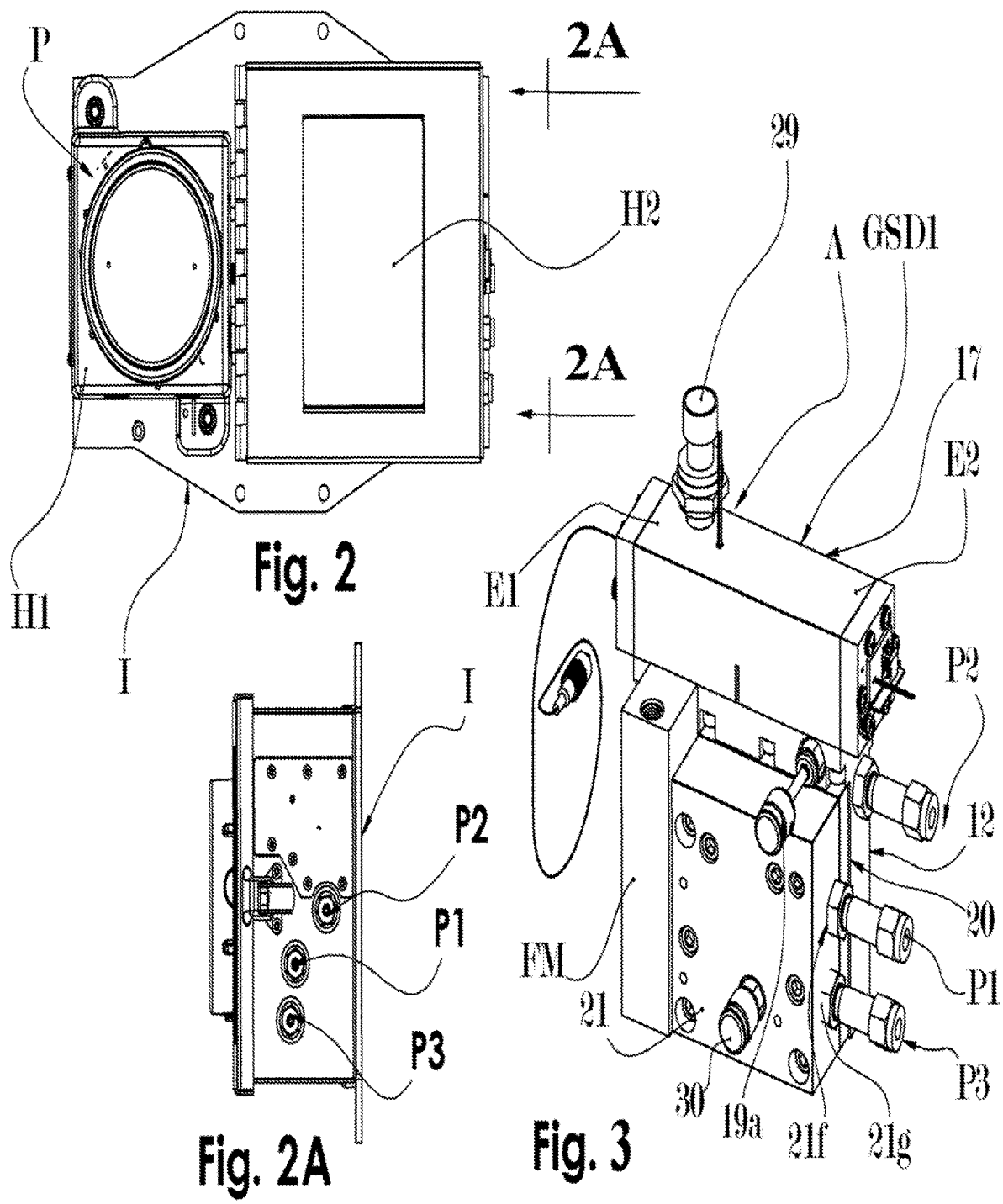

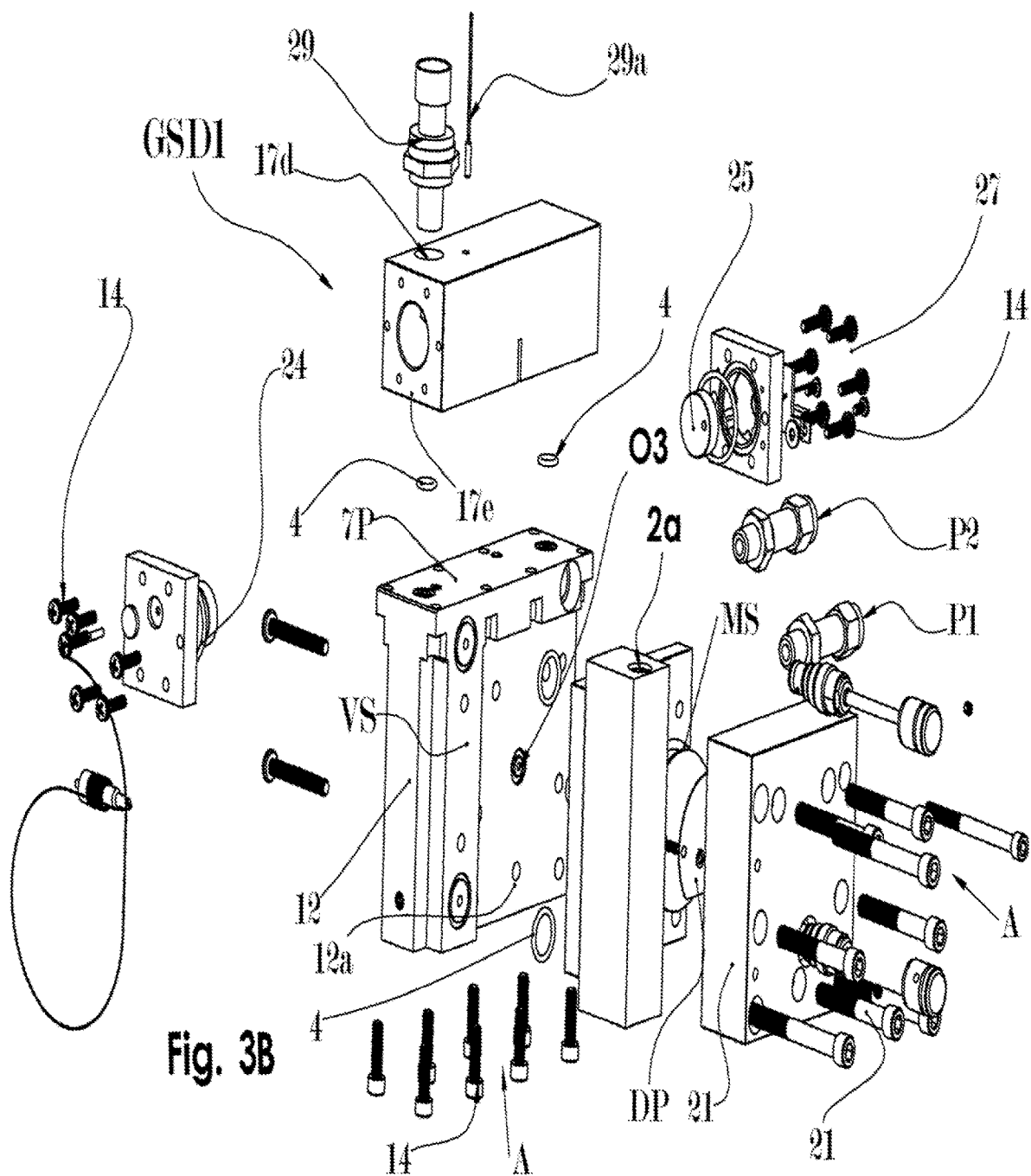

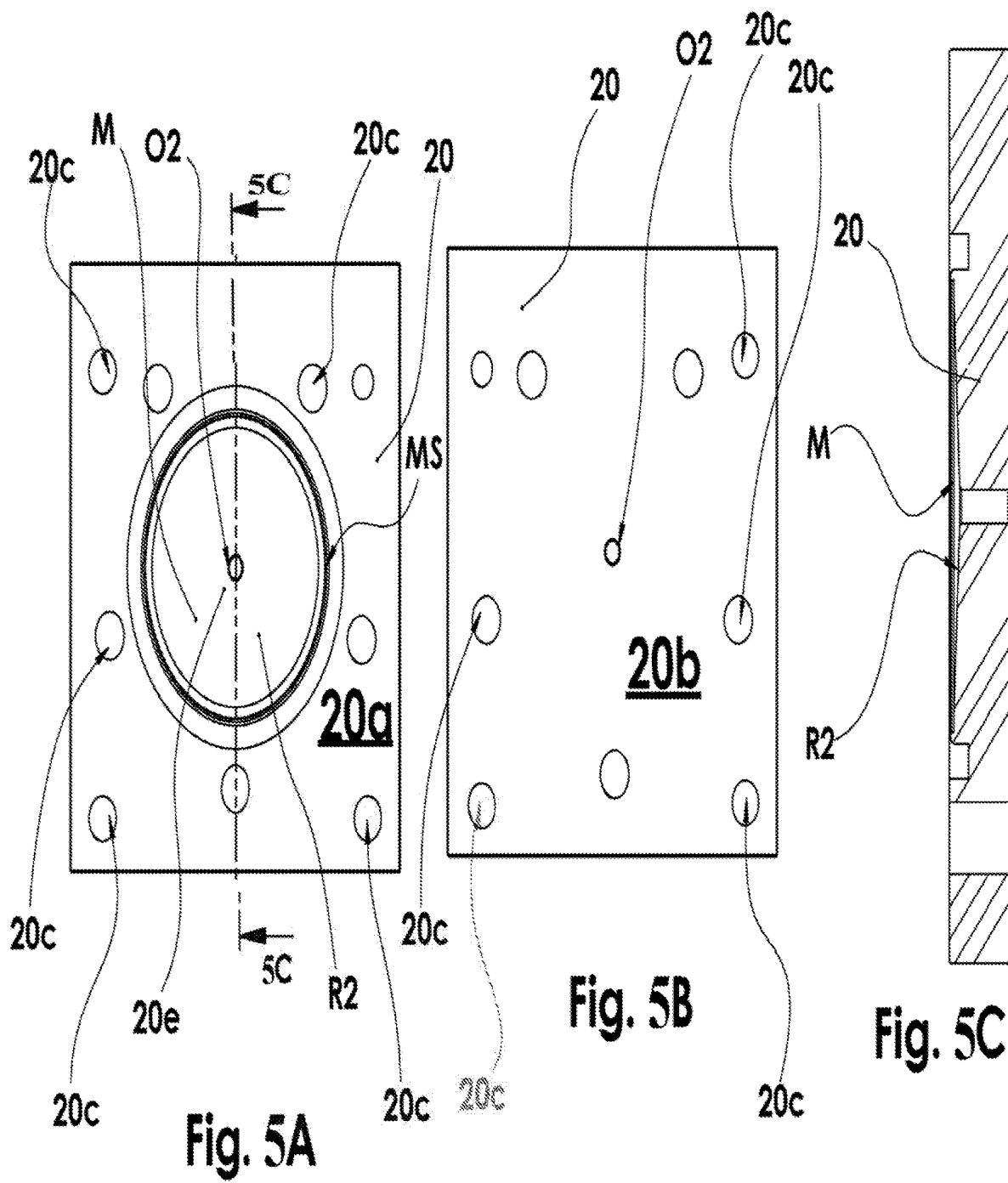

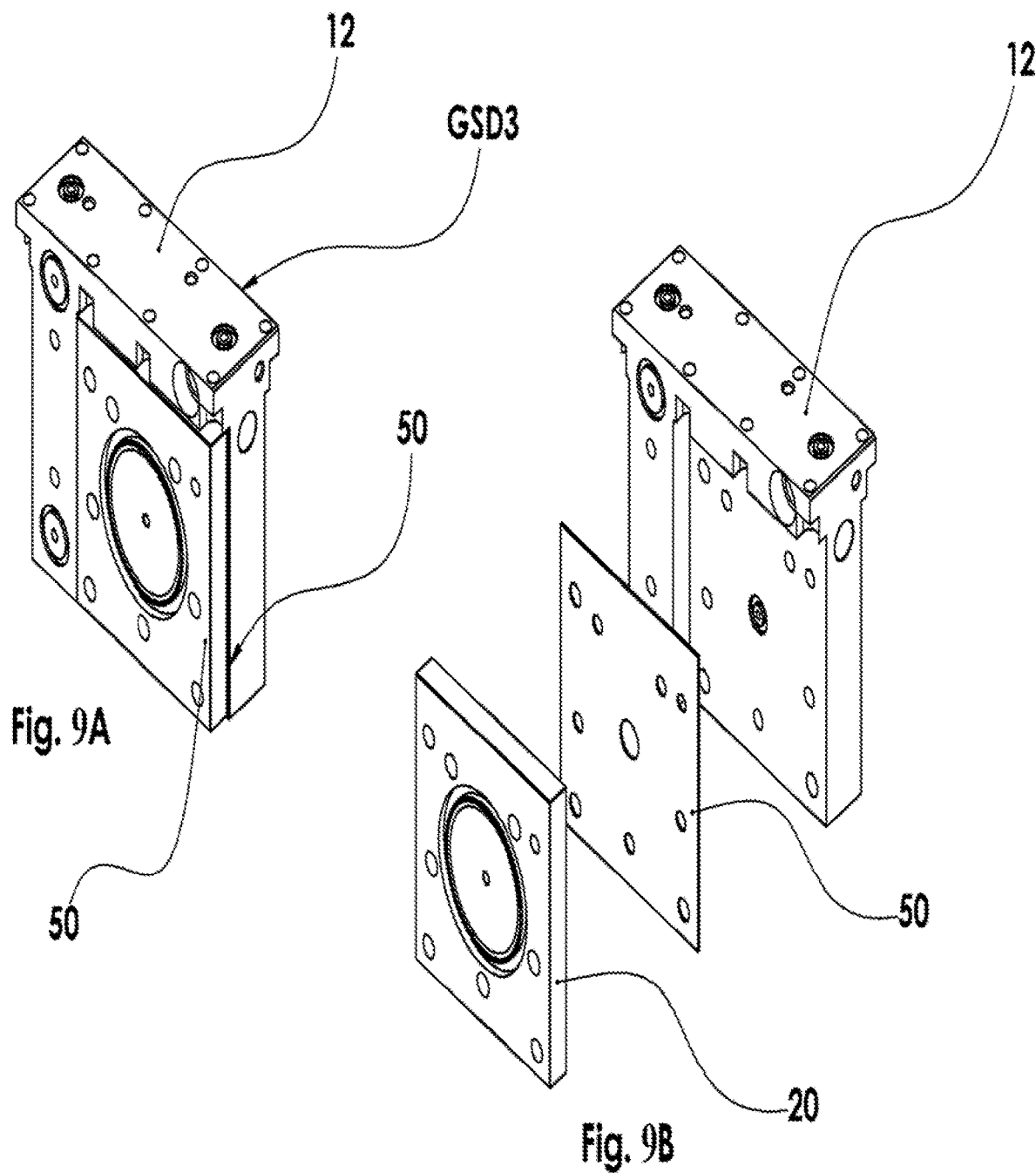

GAS SAMPLING DEVICE AND METHOD

INCORPORATION BY REFERENCE

This is a non-provisional utility patent application that claims the benefit under 35 USC 119(e) of U.S. Provisional Patent Application No. 62/480,499, entitled "Gas-Sampling Device and Method," filed Apr. 2, 2017, and U.S. Provisional Patent Application No. 62/480,322, entitled "Trace Moisture Analyzer Instrument and Method Of Detecting Trace Moisture Levels in a Gas", filed Mar. 31, 2017. These related applications are incorporated herein by reference and made a part of this application. If any conflict arises between the disclosure of the invention in this non-provisional application and that in the related provisional applications, the disclosure in this non-provisional application shall govern. Moreover, any and all U.S. patents, U.S. patent applications, and other documents, hard copy or electronic, cited or referred to in this application are incorporated herein by reference and made a part of this application.

DEFINITIONS

The words "comprising," "having," "containing," "holding," and "including," and other grammatical forms thereof, are intended to be equivalent in meaning and be open ended in that an item or items following any one of these words is not meant to be an exhaustive listing of such item or items, nor meant to be limited to only the listed item or items.

The word "rectangular" includes square.

The word "block" means a rigid structure that is capable of being acted upon to form therein a gas passageway, or a plurality of rigid structures that may be assembled into a compact, rigid assembly having therein a gas passageway.

The words "block member" means either a single, unitary block or a plurality of assembled blocks forming a compact, rigid assembly.

BACKGROUND

Gas sampling devices are used in many applications such as, for example, in the natural gas industry where they are used on pipelines, storage vessels, and gas processing equipment. These gas sampling devices have the primary function of removing any entrained liquids and particle contaminants from the gas stream and regulating the flow rate of the gas into a gas analyzer that measures some property of the gas. In the natural gas industry, the analyzers are often measuring water vapor, oxygen, hydrogen sulfide or other gas contaminants in the natural gas.

Conventional gas sampling devices use multiple components such as valves, flow meters, liquid separators, and filters that are joined and sealed together by tubing, threaded joints, and compression fittings. These devices are constantly subject to possible leakage at the locations where the joints or fittings are poorly sealed. In the typical arrangement there are ten or more fittings that could leak at either the compression side or the threaded side. In addition, the tubing results in the creation of lengthy, inefficient gas flow paths that have a high surface area and often include dead spaces. In the typical arrangement there is about four feet of tubing connecting the components. Liquids and other contaminants, especially water and hydrogen sulfide, tend to stick to those surfaces and collect in the dead spaces where there is insufficient flow to keep them entrained. Liquids that are collected in the pipes and tubing will not reach the analyzer for measurement. The collected liquids and/or contaminants on the surfaces and in the dead spaces can unexpectedly and unwantedly diffuse into the gas stream over time and produce false readings in the analyzer. As a specific example of this, during colder times of the day some of the water vapor may adsorb onto the pipes and tubing and the analyzer will read a lower value for water vapor in the gas. At warmer times this adsorbed water vapor may be released into the gas stream and give a higher reading. Therefore, it is desirable to minimize the surface area and dead zones in the gas sampling device.

SUMMARY

The gas sampling device and method disclosed herein are intended to reduce or eliminate the short comings of conventional gas sampling devices as discussed above by minimizing the number of threaded and/or compression connections and minimizing the surface area exposed to the gas. As a result, the gas sampling device is less likely to have leaks and less liquid is collected on surfaces exposed to the gas. The embodiments described here are specifically a minimal design for sampling natural gas for analysis of its water vapor content. However, the construction techniques described herein may also be employed advantageously for other types of sampling systems, for example, oxygen, hydrogen sulfide and other gases in natural gas. Also, other types of components could be added to the sampling device if required for special circumstances, for example, a flow meter. The addition of such components may be accomplished using the same seal connection structure along the gas passageway disclosed herein.

The gas sampling device and method disclosed herein have one or more of the features depicted in the embodiments discussed in the section entitled "DETAILED DESCRIPTION OF SOME ILLUSTRATIVE EMBODIMENTS." The claims that follow define the gas sampling device and method diclosed herein, distinguishing them from the prior art; however, without limiting the scope of the gas sampling device and method as expressed by these claims, in general terms, some, but not necessarily all, of their features are:

One, the gas sampling device comprises a block member that includes a gas passageway that defines a flow path for the gas from a gas inlet to a gas outlet through the block member. Along the flow path is a liquid separator including a porous membrane that acts as a barrier to any liquid in the gas being sampled, allowing gas to flow through the membrane and into a passageway segment downstream of the membrane. Along the flow path is a gas analyzer and a metering valve system that controls the flow of gas through the device. A liquid bypass flow passageway, separate from the gas flow path, is in communication with the liquid separator and allows liquid to exit the gas sampling device.

In one embodiment a liquid separator block member and a gas analyzer block member are connected together and include a gas passageway through the members and the metering valve system from an inlet to an outlet along a predetermined flow path through the device. The gas analyzer block member and liquid separator block member are adjacent and in contact with each other and each include a passageway leg terminating in an opening in an exterior face of a block member. The flow path proceeds from the inlet through the liquid separator block member, and then through the gas analyzer block member and out the outlet through sealed connection points along the passageway where faces of the adjacent gas analyzer and liquid separator block members abut and contact each other with the openings in their respective faces aligned. The flow path for gas comprises passageway legs that have contiguous terminal openings that are aligned and interconnected at any abutting block surfaces. There is a seal at the terminal openings of interconnecting passageway legs that prevents gas from leaking as the gas moves along the flow path. Thus, tubing and tubing connections are eliminated. Typically, the flow path has a length that is less than 36 inches in one embodiment. The passageway mainly has a cylindrical configuration with a diameter of less than 0.50 inch in one embodiment. The device disclosed herein is compact, and in one embodiment, has a length less than 16 inches, a depth less than 16 inches, and a height less than 16 inches.

Two, the liquid separator block member has a liquid collection chamber along the gas flow passageway upstream of the porous membrane. This liquid collection chamber has a collection zone in which any liquid in the gas is collected and exits the device along the bypass passageway. A deflection plate directs any liquid in the gas downward into a lower sink zone of the liquid collection chamber from which the liquid exits from the liquid separator block along a bypass passageway. The porous membrane is within the chamber and is sealed so gas exiting the liquid collection chamber flows through the membrane. The membrane may have a hydrophobic surface positioned to contact the gas as it initially flows through the membrane.

Three, the gas passageway may have three passageway legs: A first passageway leg in one block in communication with the inlet allows gas to flow into the first passageway leg along a continuous flow path terminating in the liquid collection chamber. A second passageway leg in the gas analyzer block is in communication with the liquid collection chamber so that gas exiting the liquid collection chamber may flow directly into and through the sealed porous membrane downstream of and adjacent to the deflection plate. A third passageway leg in the second block downstream of the membrane is in communication with the outlet to allow gas to exit the device. Any liquid collected exits the device through the liquid bypass flow passageway.

Four, the metering valve system may include a pair of valves: A first manually operable valve is mounted to and sealed in the block member and seated along the liquid bypass flow passageway so that liquid in the liquid collection chamber flows from the block member under the control of the first valve. A second manually operable valve is mounted to and sealed in the block member and seated along the passageway downstream of the liquid collection chamber. This valve regulates the flow of gas through the device.

Five, along the flow path is a light transmission pathway over which light from a laser propagates. The gas passageway expands into an enlarged chamber that functions as a light transmission zone through which the laser light propagates along its light transmission pathway making multiple passes. A light collection system including a light detector positioned to collect the laser light after such light makes multiple passes through the light transmission zone. The light collection system may be a pair of mirrors, one mirror mounted at one end of the light transmission pathway and the other mirror mounted at the other end of the light transmission pathway. The mirrors are shaped to reflect multiple passes of light between the mirrors, and at one end of the said one block a lens that focuses light on the mirror at the other end of the said one block. A light detector near one end of light transmission pathway is positioned to collect light after multiple reflections of the light off the mirrors.

Six, the device may also include a flow meter. For example, the flow meter may be in the bypass flow path of the device. In one embodiment the flow meter is in a segment of the flow path that is downstream of the light transmission zone and upstream of the outlet from the device. The flow meter has an inlet into which gas exiting the light transmission zone enters the flow meter and an outlet from which gas exits the flow meter and flows along another segment of the passageway and out the outlet. Alternately, the flow meter may be in the bypass flow path of the device or downstream of the gas outlet. The method of sampling a gas disclosed herein comprises feeding the gas along a flow path having a length that is less than 36 inch in one embodiment. The flow path comprises a sealed passageway within a compact block member having a length less than 16 inches, a depth less than 16 inches, and a height less than 16 inches in one embodiment. The block member has a built-in liquid collection chamber along the flow path that separates any liquid in the gas being sampled. The liquid collection chamber includes a sealed porous membrane along the flow path downstream of and adjacent to a deflection plate. The membrane acts as a barrier to liquid, allowing gas to flow through the membrane and into a portion of the passageway downstream of the membrane.

These features are not listed in any rank order nor is this list intended to be exhaustive.

DESCRIPTION OF THE DRAWINGS

Some embodiments of the gas sampling device and method are discussed in detail in connection with the accompanying drawing, which is for illustrative purposes only. This drawing includes the following figures (FIGS.), with like numerals and letters indicating like parts:

FIG. 2 is a front view of a trace moisture analyzer instrument using the gas sampling device depicted in FIG. 3.

FIG. 2A is a side view of the instrument shown in FIG. 2 taken along line 2A-2A of FIG. 2.

FIG. 3 is a perspective view of one embodiment of the gas sampling device.

FIG. 3B is an exploded right hand perspective view of the embodiment of the gas sampling device shown in FIG. 3.

FIG. 5A is a side view of an intermediate block of the one embodiment of the gas sampling device shown in FIG. 3 looking at one side of the intermediate block.

FIG. 5B is a side view of the intermediate block shown in FIG. 5A looking at the other side of the intermediate block.

FIG. 5C is a cross-sectional view taken along line 5C-5C of FIG. 5A.

FIGS. 9A and 9B depict a third embodiment comprising an assembly of blocks using a unitary seal sandwiched between blocks

DETAILED DESCRIPTION OF SOME ILLUSTRATIVE EMBODIMENTS

Prior Art

Figure 1:
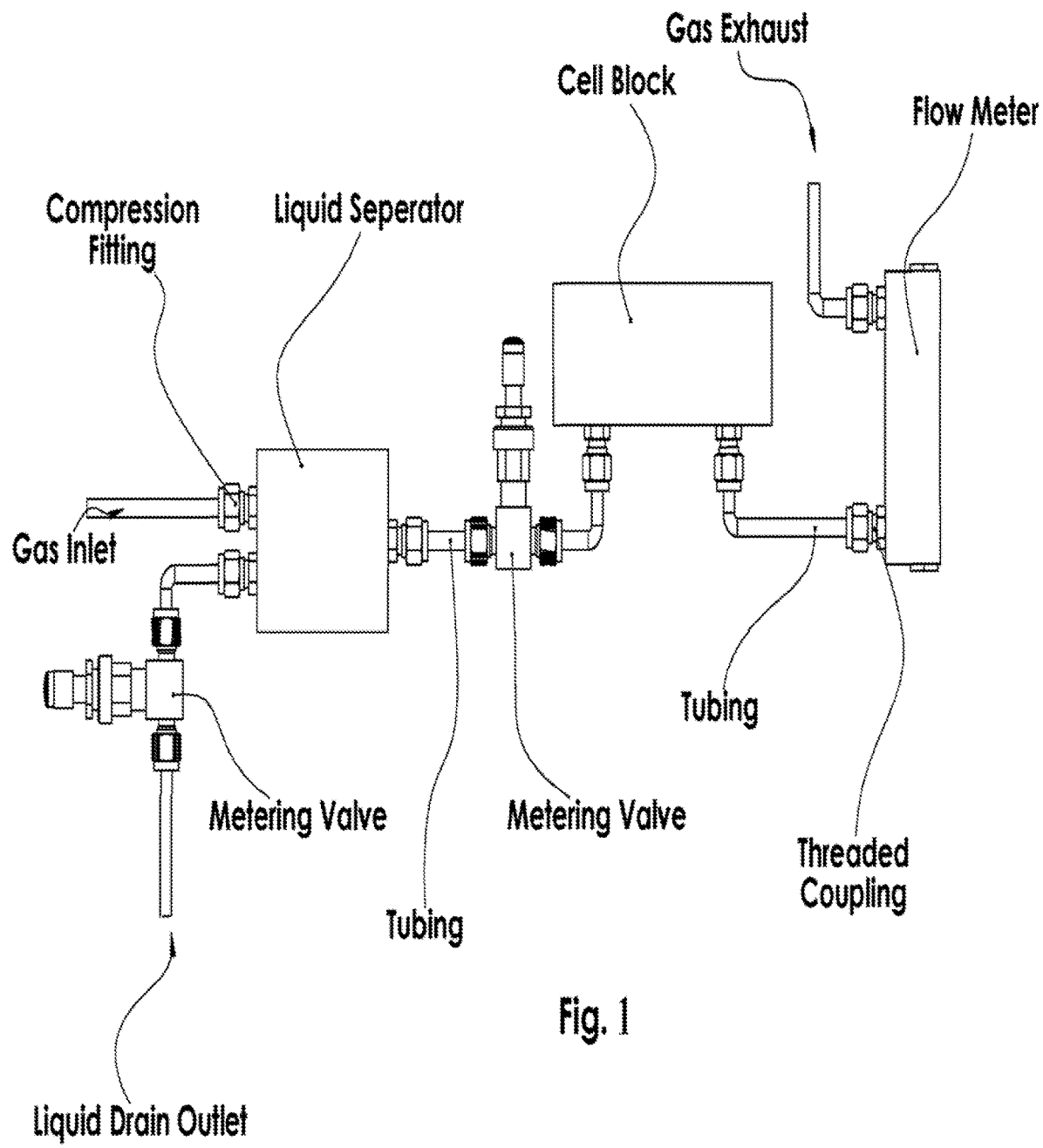
FIG. 1 is a schematic illustration of a prior art gas sampling device.

As illustrated in FIG. 1, a conventional gas sampling device uses multiple components such as metering valves, flow meters, and liquid separators that are joined and sealed together by tubing, threaded couplings, compression fittings, etc. Such a bulky conventional device is constantly subject to possible leakage at the locations where the joints or fittings are poorly sealed.

Moisture Analyzer:

As illustrated in FIGS. 2 and 3, a moisture analyzer instrument, designated by the letter I, has two separate housings: housing H1 for a laser package P and housing H2 for the explosion resistant gas sampling device GSD1 (FIG. 3). Because of the electrical connections to the electronic components of the laser package P, there is a risk of sparking that could ignite any explosive gas being sampled and tested. By using the compact, separate explosion resistant gas sampling device GSD1 that does not employ any internal electrical components that could be a source of ignition and is internally sealed to prevent gas leaks, the likelihood of an explosion in the gas sampling device GSD1 is essentially eliminated.

Gas Sampling Device:

General

Three embodiments of the gas sampling device are depicted in the drawing: The first embodiment (FIGS. 3 through 7K) comprises an assembly of blocks and is designated by the alphanumeric symbol GSD1; the second embodiment (FIGS. 8A and 8B) comprises a unitary block and is designated by the alphanumeric symbol GSD2; the third embodiment (FIGS. 9A and 9B) comprises an assembly of blocks using a unitary seal sandwiched between a pair of blocks and is designated by the alphanumeric symbol GSD3.

FIGS. 3 through 7K

As best shown in FIGS. 3, 3A, 3B, 3C and 3D, the gas sampling device GSD1 includes a plurality of blocks: a base block 12, a cell block 17, an intermediate block 20, and an outer block 21. A flow meter FM is also adapted to be attached to the blocks. These blocks 12, 17, 20, 21 and flow meter FM are fastened together into an assembly A with adjacent blocks having planar surfaces abutting each other. As best depicted in FIG. 3E, there is a main gas flow path FP for a sample gas through the assembly A extending from an inlet opening 21*f* in the outer block 21 to an outlet opening 12*a* in the base block 12 as depicted by the arrow a. This main gas flow path FP comprises passageway segments or legs L1 through L7 in the blocks 12, 17, 20, and 21 and flow meter FM that have contiguous terminal openings at ends of some segments or legs of the passageways. These terminal openings are aligned and interconnected at abutting block surfaces to enable the sample gas to flow along the flow path FP between the blocks 12, 17, 20, 21 and flow meter FM. An O-ring seal 4 at the terminal opening in passageway legs L1 through L7 seals the aligned and interconnecting passageway legs to prevent gas from leaking at the interconnections of these passageways legs as the gas travels along the flow path FP.

Figure 3A:
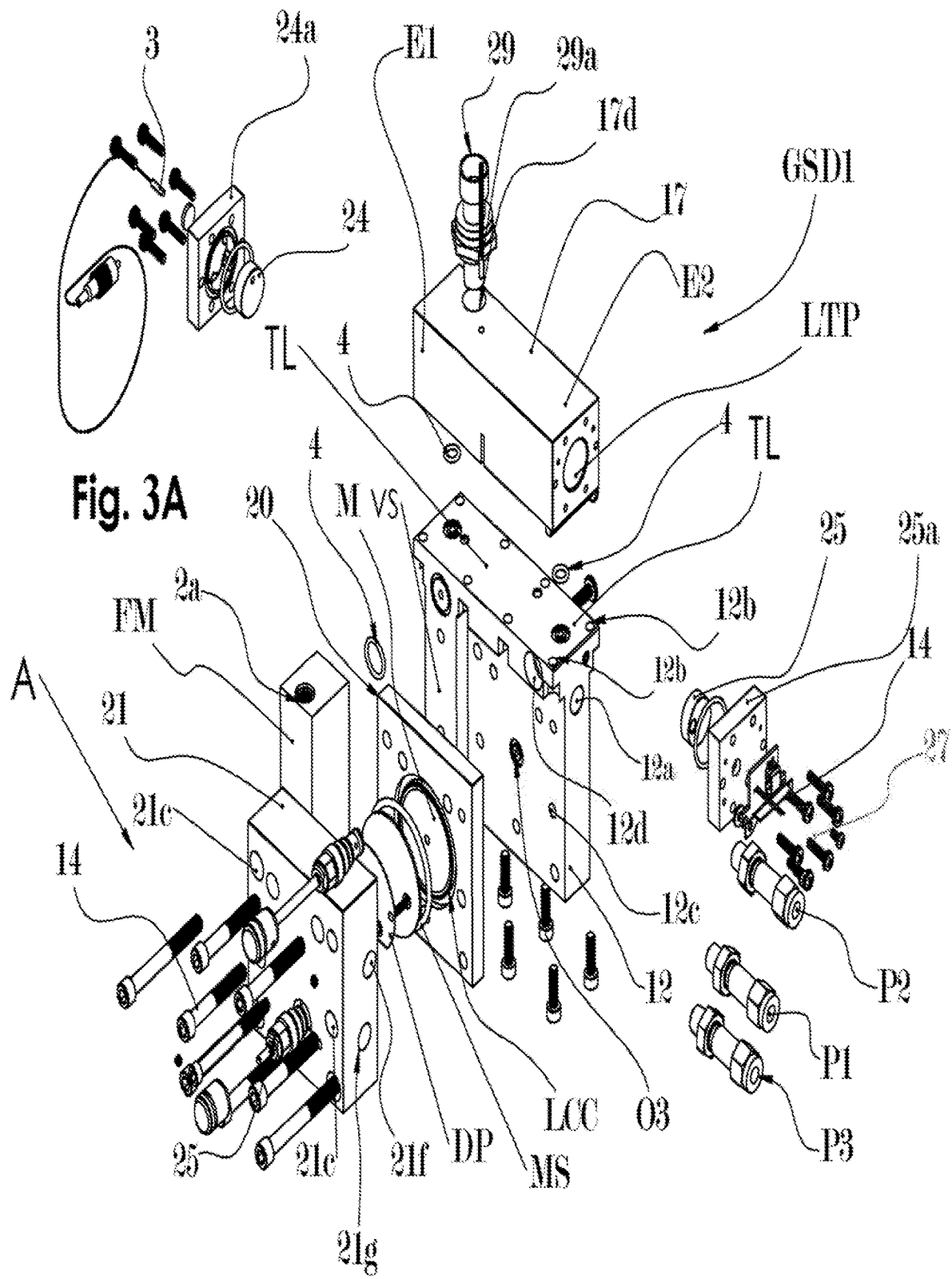
FIG. 3A is an exploded left hand perspective view of the embodiment of the gas sampling device shown in FIG. 3.
Figure 3C:
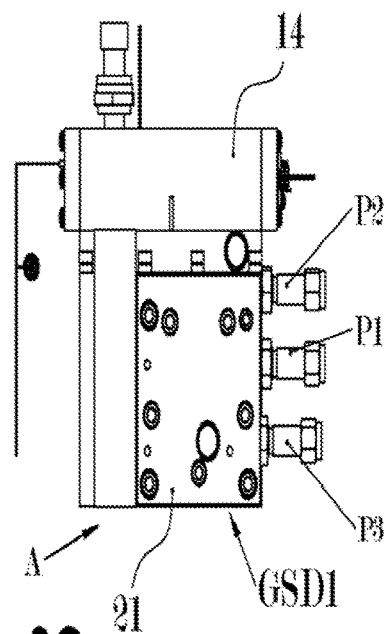
FIG. 3C is a side view of the embodiment of the gas sampling device shown in FIG. 3.
Figure 3D:
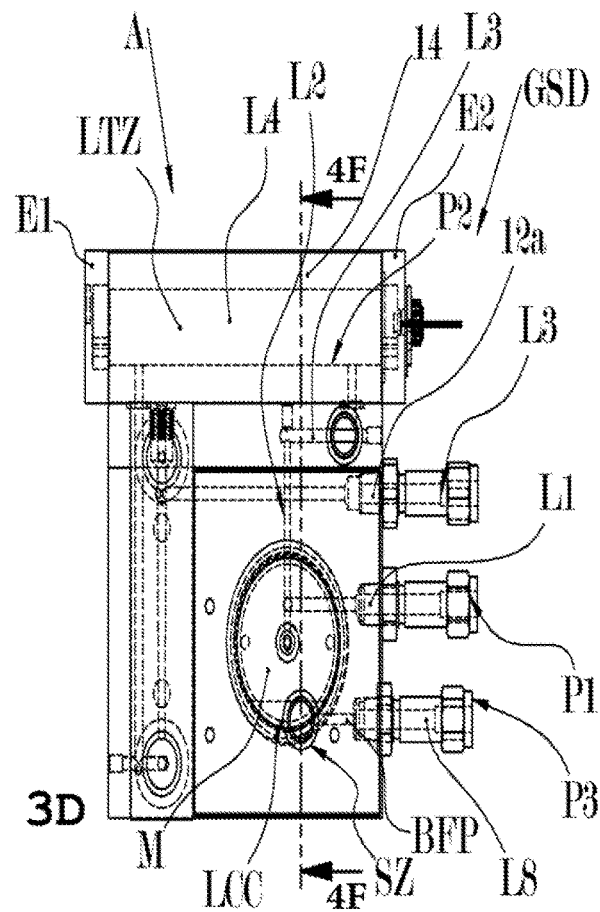
FIG. 3D is a side view schematically depicting in dotted lines the flow path of gas through the gas sampling device shown in FIG. 3.
Figure 4E:
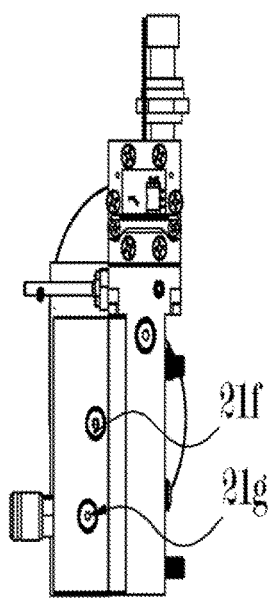
FIG. 4E is an end view of the outer block shown in FIG. 3C.
Figure 4F:
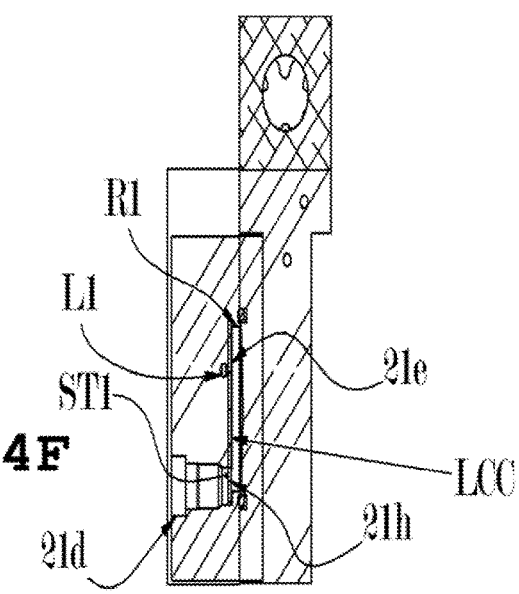
FIG. 4F is a cross-sectional view taken along line 4F-4F of FIG. 3D.
Figure 3E:
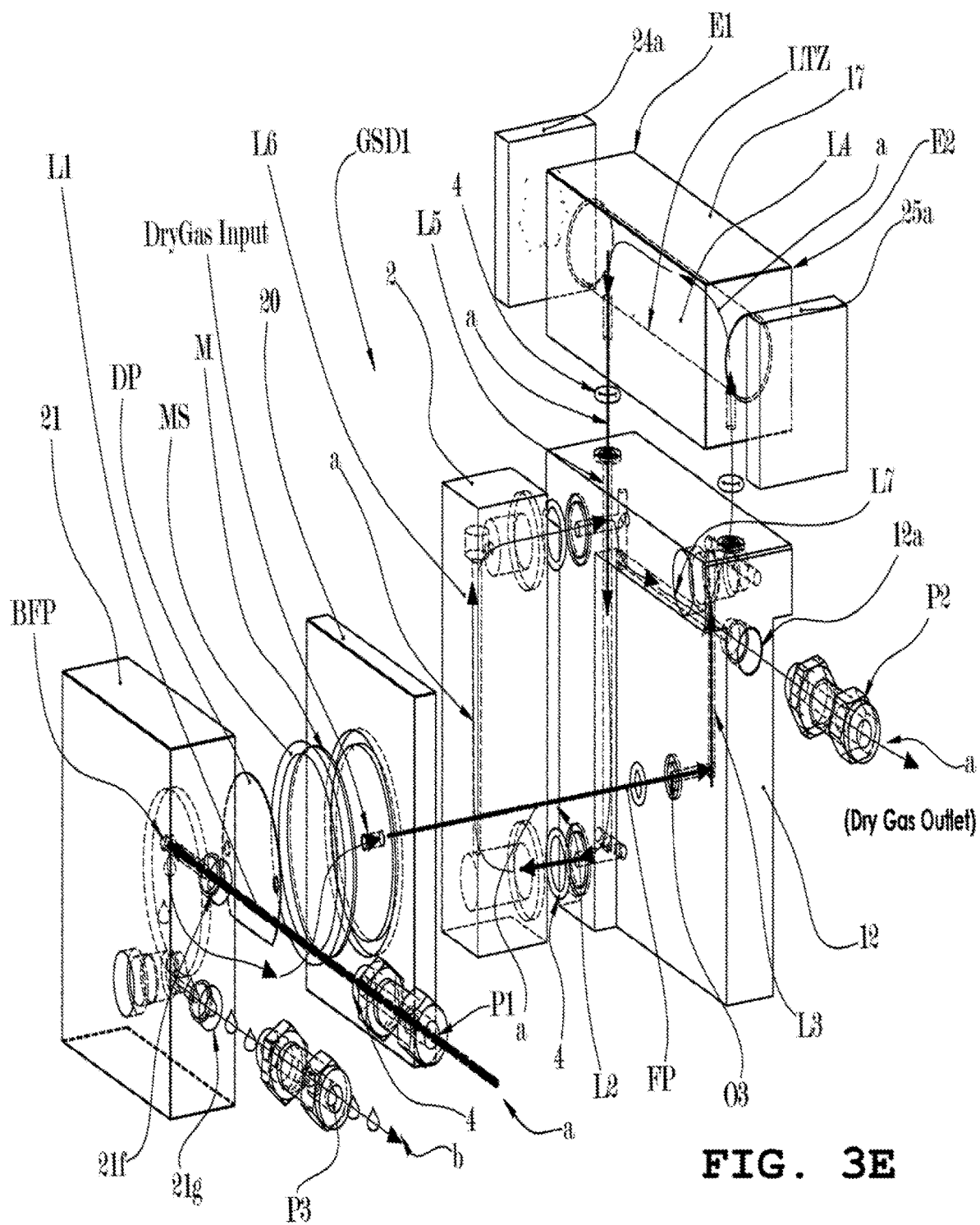
FIG. 3E is a schematic illustration of the flow path of gas through the gas sampling device shown in an explosion view.
Figure 4A:
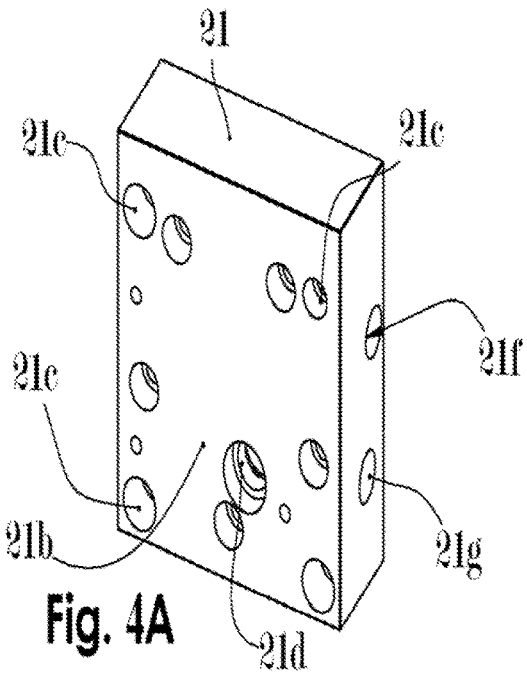
FIG. 4A is a left hand perspective view of an outer block of the one embodiment of the gas sampling device shown in FIG. 3 looking at an outer surface.
Figure 4B:
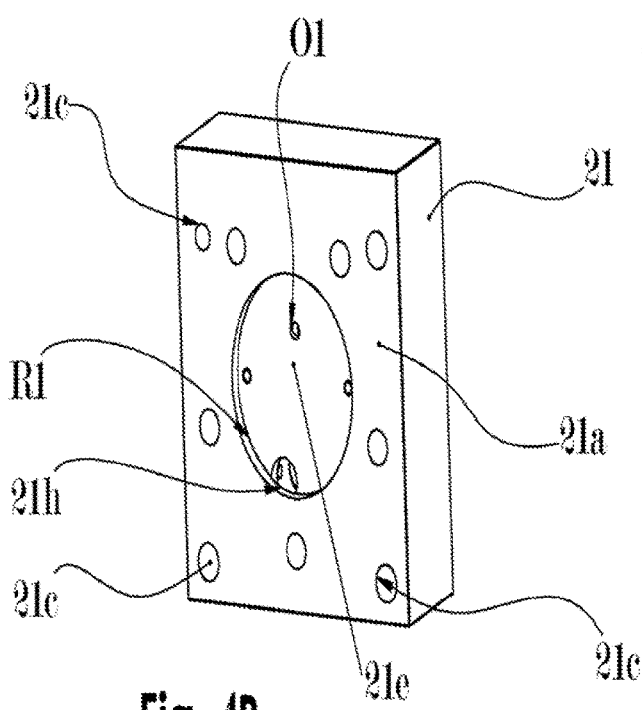
FIG. 4B is a left hand perspective view of the outer block shown in FIG. 4A looking at an inner surface.
Figure 4C:
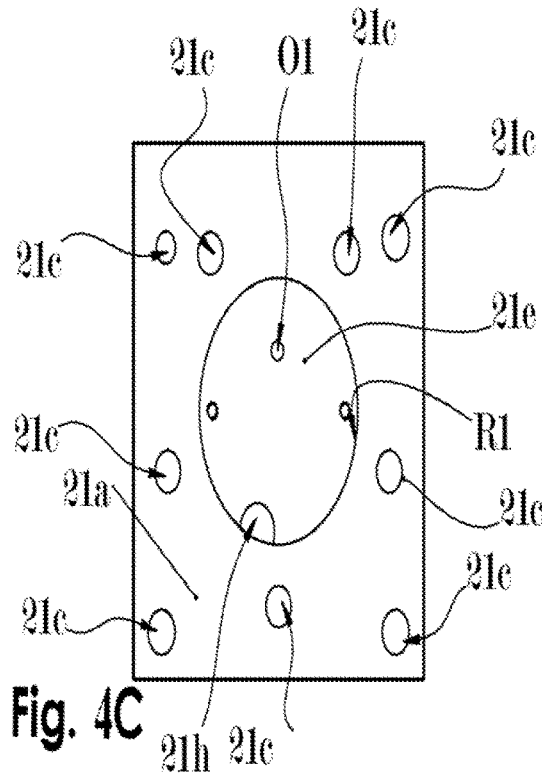
FIG. 4C is a side view of the outer block shown in FIG. 4B.
Figure 4D:
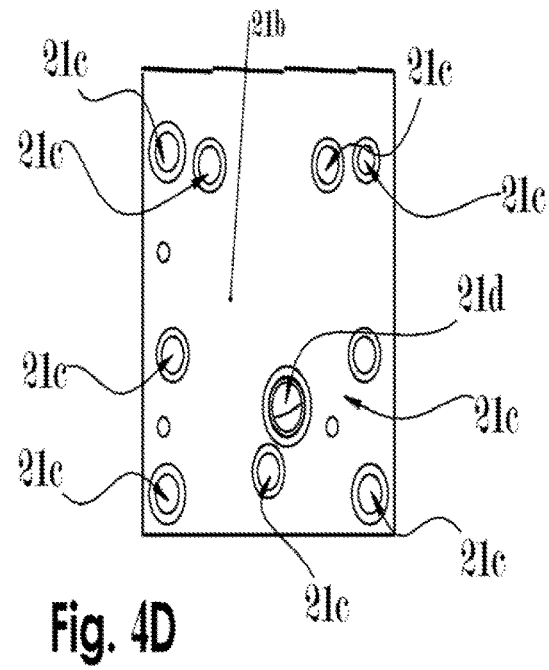
FIG. 4D is a side view of the outer block shown in FIG. 4A.
Figure 6A:
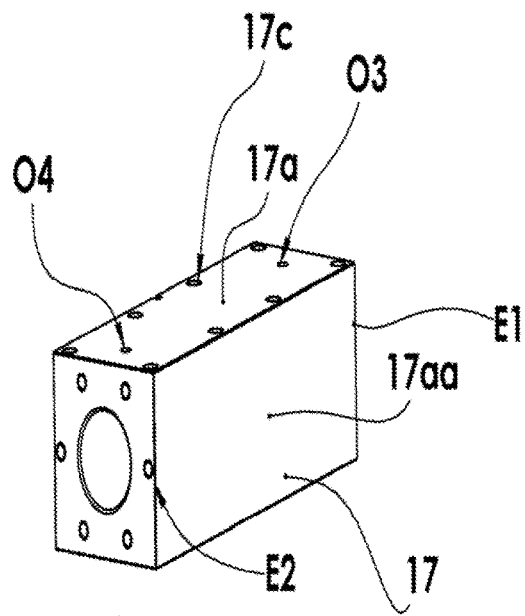
FIG. 6A is a left hand perspective view of a cell block of the one embodiment of the gas sampling device shown in FIG. 3 looking at its bottom surface.
Figure 6C:
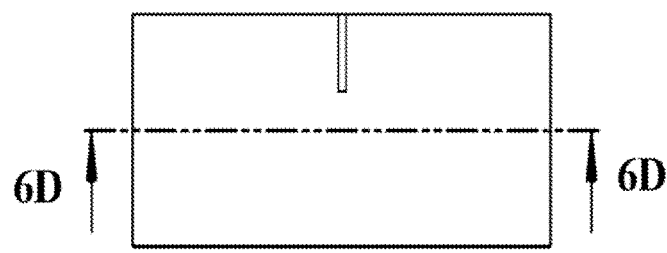
FIG. 6C is a side view of cell block shown in FIG. 6B.
Figure 6B:
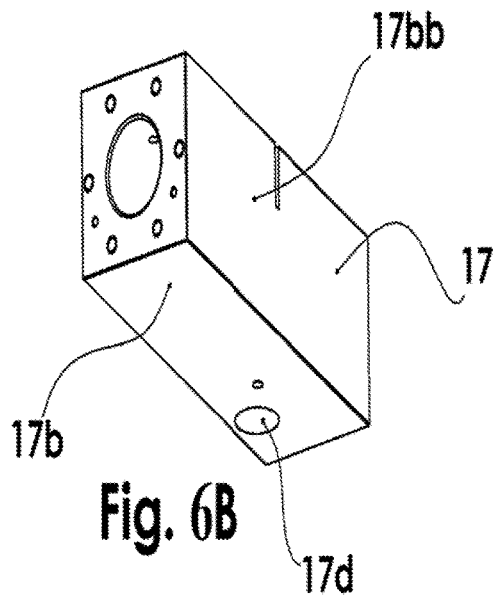
FIG. 6B is a left hand perspective view of a cell block of the one embodiment of the gas sampling device shown in FIG. 3 looking at its top surface.
Figure 6D:
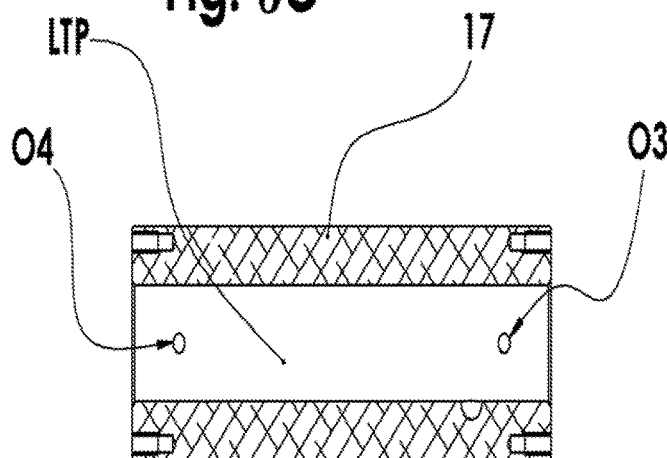
FIG. 6D is a cross-sectional view taken along line 6D-6D of FIG. 6C.
Figure 7A:
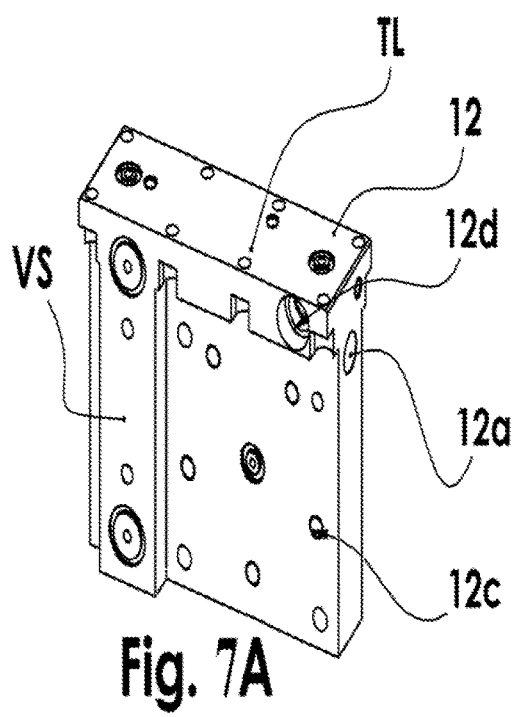
FIG. 7A is a left hand perspective view of a base block of the one embodiment of the gas sampling device shown in FIG. 3 looking at one side.
Figure 7C:
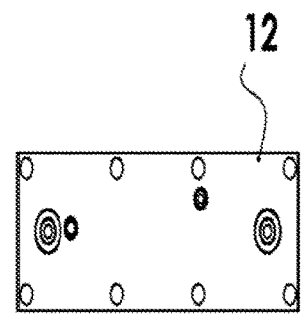
FIG. 7C is a top view of the base block shown in FIG. 7A.
Figure 7D:
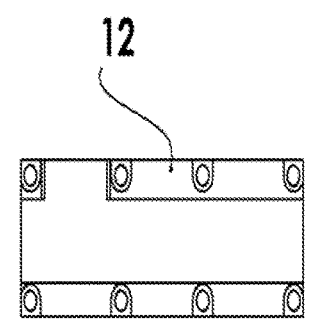
FIG. 7D is a bottom view of the base block shown in FIG. 7A.
Figure 7B:
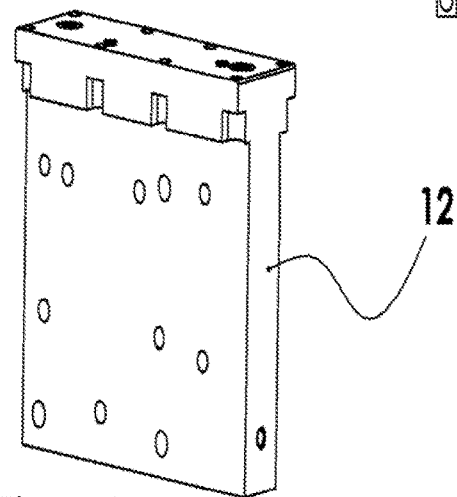
FIG. 7B is a left hand perspective view of a base block of the one embodiment of the gas sampling device shown in FIG. 3 looking at its other side.
Figure 7E:
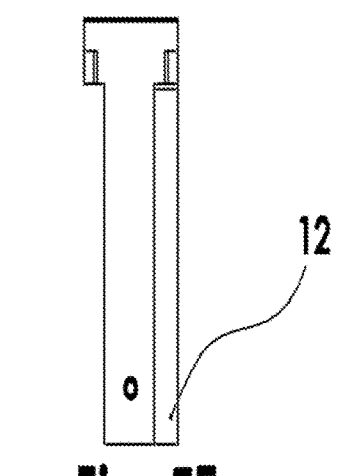
FIG. 7E is a right hand view of the base block shown in FIG. 7B.
Figure 7F:
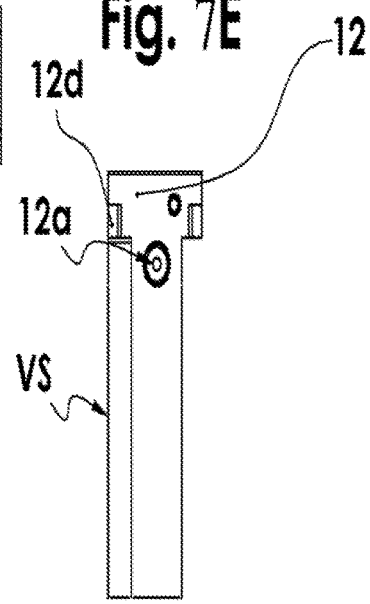
FIG. 7F is a right hand end view of the base block shown in FIG. 7A.
Figure 7G:
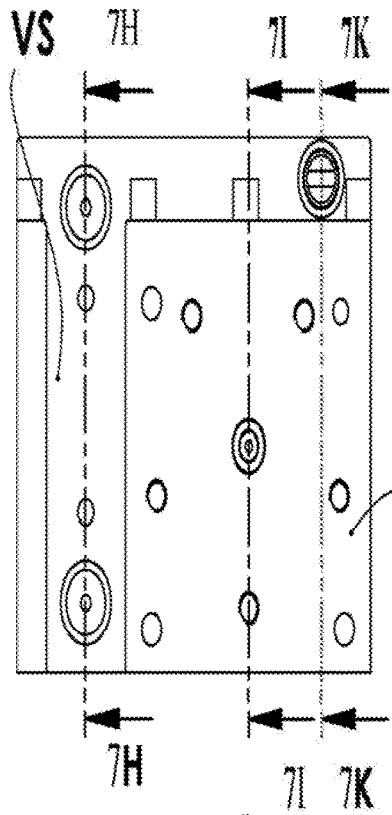
FIG. 7G is a side view of the base block shown in FIG. 7A.
Figure 7H:
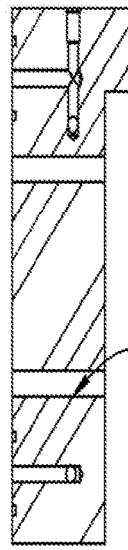
FIG. 7H is a cross-sectional view taken along line 7H-7H of FIG. 7G.
Figure 7I:
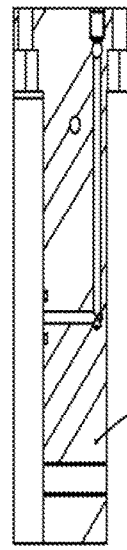
FIG. 7I is a cross-sectional view taken along line 7I-7I of FIG. 7G.
Figure 7K:
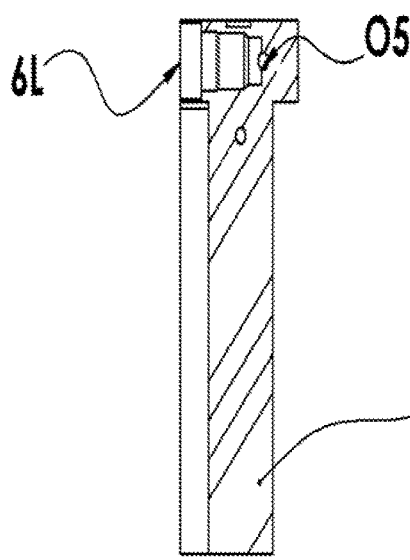
FIG. 7K is a cross-sectional view taken along line 7K-7K of FIG. 7G.

A liquid collection chamber LCC (FIGS. 3A and 3D) within the assembly A is formed between the inside abutting surfaces of the adjacent blocks 20 and 21. The liquid collection chamber LCC is along the flow path FP and has therein a vertically oriented, semi-circular deflection plate DP that collects liquid on a surface of the plate. Typically, this deflection plate DP is made of metal. This collected liquid flows downward into a lower sink zone SZ (FIG. 3D) of the liquid collection chamber LLC. A porous membrane M is along the flow path FP downstream of and adjacent to the deflection plate DP. This membrane M is stretched taut like a drumhead and sealed with an O-ring seal MS (FIG. 3E). This membrane M acts as a barrier to liquid, allowing gas to flow through the membrane and into passageway legs downstream of the membrane.

The cell block 17 includes a passageway leg L4 that functions as a light transmission pathway LTP along the flow path FP that is downstream of the membrane M and through which light from a laser (not shown) is adapted to propagate. The passageway leg L4 that functions as a light transmission pathway LTP expands into an enlarged cylindrical chamber that functions as the light transmission zone LTZ (FIG. 3E). The cell block 17 may be a Herriott cell having a pair of mirrors 24 and 25 (FIG. 3A), one mirror 24 mounted at a far end of the light transmission pathway LTP and the other mirror 25 mounted at the near end of the light transmission pathway. The mirrors 24 and 25 are shaped to reflect multiple passes of light between the mirrors. At one end E1 of the cell block 17 is a lens 3 that focuses light on the mirror 25 at the other end E2 of the cell block. A light detector 27 (FIG. 3A) near the end E2 of the cell block 17 is positioned to collect light after multiple reflections of the light off the mirrors 24 and 25.

The blocks are assembled as follows: The intermediate block 20 is disposed between the outer block 21 and base block 12, and the cell block 17 is mounted on a top ledge TL of the base block 12. Conventional screws 14 fasten together these blocks 12, 17, 20 and 21 into the assembly A. Typically, the blocks 12, 17, 20, and 21 are electrolysis nickel-plated aluminum. These blocks 12, 17, 20, and 21 have rectangular shaped side portions with adjacent side portions at right angles to each other. The surfaces of the side portions are smooth so that abutting surfaces are flush with each other and tightly bear against each other upon tightening fasteners, namely, the screws 14. As shown in FIG. 3E, the passageway legs L1 through L7 of interconnecting passageways forming the main flow path FP are sealed at junction points by O-rings 4. Thus, there is no gas seepage between the surfaces of planar side portions in contact with each other.

Outer Block

As shown best in FIGS. 3 and 3E, the outer block 21 includes an inlet port compression fitting P1 for the sample gas being tested. The fitting P1 is inserted into the inlet opening of the main flow path FP, shown by the arrow a. A bypass flow passageway BFP shown by the arrow b in FIG. 3E allows any liquid in the sink zone SZ of the liquid collection chamber LCC to exit the gas sampling device GSD1 at an outlet exit 21g in the outer block 21. A bypass port compression fitting P3 is inserted into the exit opening 21g.

As best depicted in FIGS. 4A through 4D, the outer block 21 has an inner planar side portion 21a and an opposed, outer planar side portion 21b, a series of holes 21c along the perimeter of the outer block through which the screws 14 pass, a central circular recess R1 in the side portion 21a, and a bore opening 21d in the side portion 21b. A flow control valve 30 fits tightly into a sealed bore opening 21d with steps that decrease in diameter, with the smallest diameter, the most inner step, terminating in a semi-circular opening 21h at a floor 21e of the recess R1. Sample gas flows along a first passageway leg L1 in this outer block 21 that turns at a right angle into a terminal opening O1 (FIGS. 4B and 4C) in a floor 21e of a circular recess R1 in the inside surface of the outer block 21. The opening O1 is aligned with an opening O2 in the leg L2 in the block 20 to allow the sample gas to flow from the outer block 21 into the passageway leg L2 in the intermediate block 20. Closing the valve 30 (FIG. 3) directs all the gas entering the gas sampling device GSD1 to flow along the main flow path FP; opening the valve 30 allows a portion of the sample gas to flow through the liquid collection chamber LCC. The gas pressure blows any liquid in the sink zone SZ out the bypass port compression fitting P3.

Intermediate Block

As best depicted in FIGS. 5A through 5C, the inside surface of the intermediate block 20 includes a circular recess R2 aligned with the recess R1 upon assembly of the blocks 20 and 21. The liquid collection chamber LCC includes the deflection plate DP (FIGS. 3A and 3B) seated in the recess R1 and a membrane M (FIGS. 3A and 3B) seated in the recess R2 and sealed with an O-ring seal MS. The deflection plate DP has a diameter only slightly less than the recess R1 and its lower portion is removed so that the plate DP does not cover the opening 21h upon assembly of the blocks 20 and 21. The recess R1 and R2 are aligned to be concentric and of essentially the same diameter to form upon assembly of the blocks 20 and 21 a cylindrical hollow structure between the abutting surfaces of the blocks 20 and 17. Consequently, when the deflection plate DP is seated in the recess R1 it's severed lower portion allows collected liquid that condenses on the deflection plate DP to flow downward due to gravity into the sink zone SZ and out the gas sampling device GSD1 through a bypass flow passageway BFP (FIG.3D).

As best depicted in FIGS. 5A through 5C, the intermediate block 20 has a first planar side portion 20a and an opposed, second planar side portion 20b, a series of holes 20c along the perimeter the intermediate block, and a central circular recess R2 in the side portion 20a. In the recess R2 is a floor 20e with an orifice O2 therein at the center of the recess R2. Upon assembly of the blocks 12, 20 and 21, the tips of the screws 14 pass through the aligned holes 21c and 20c and are screwed into aligned holes 12c in the base block 12, bringing the side portions into intimate contact with each other.

The porous membrane M is seated snugly in the recesses R1 and R2 that covers the orifice O2 and acts as a barrier to liquid. Any liquid in the gas sample coalesces on the deflection plate DP and flows into sink zone SZ. The sample gas flows into the gas sampling device GSD1 through the gas inlet port compression fitting P1 along the machined passageway leg L1 in the block 21 through the membrane M and through the opening O2 along a passageway leg L2 into an opening O3 in the block 12 to turn upward at a right angle into the machined passageway leg L3 in the block 12.

Mirror Mounting Elements

As shown in FIG. 3E, a mirror mounting element 24a attaches a first concave mirror 24 to the end E1 of the cell block 17 and a mirror mounting element 25a attaches a second concave mirror 25 to the end E2 of the cell block 17. These concave mirrors 24 and 25 are shaped to make multiple reflections of light between the mirrors, thereby increasing the optical path length that a laser beam of light transverses prior to striking a photo-detector assembly 27 at the end E2 of the cell block 17. The light beam is at a wavelength in the near infrared range of 1871 nanometers (nm) and is focused on the mirror 25 by a lens 3 (FIG. 3A) near the end E1 of the cell block 17. As disclosed in U.S. Provisional Patent Application No. 62/480,322, a suitable laser light package is discussed that may be used with the gas sampling device GDS1 shown in FIG. 3A.

Cell Block

As best depicted in FIGS. 6A through 6D, the cell block 17 has a first planar bottom side portion 17a and an opposed, second planar top side portion 17b, a series of bore opening 17c along the perimeter of the bottom side portion 17a, first and second opposed ends E1 and E2, opposed planar side portions 17aa and 17bb, and an opening O3 at the end E1 and an and opening O4 at the end E2. The screws 14 extending through holes 12b in the top ledge TL of the base block 12 fasten the cell block 17 to the top of the block 12. Sample gas flowing from the base block 12 enters a passageway leg L4 extending between the orifices O3 and O4 in the cell block 17. As shown best in FIG. 3A, a pressure transducer 29 fits snug, and is sealed, in the opening 17d in the top of the cell block 17. A thermistor 29a (FIG. 3A) adjacent the transducer 29 and extending into the flow path detects the temperature within the cell block 17. The laser light from an output of a laser diode (not shown) is directed to the lens 3 by means of a fiber optic cable (not shown).

Base Block

As best shown in FIGS. 7A through 7K, the base block 12 has a generally T-shaped cross-section with a flat top planar surface to which the cell block 17 is mounted as discussed above. A compression fitting P2 inserted into the outlet opening 12a in a side of the base block 12 provides an exit for the gas leaving the assembly A. The flow meter FM is fastened to the base block's planar vertical surface VS that is offset to a side of the assembly A. Gas exiting the orifice O4 in the cell block 12 flows along the passageway leg L5 in the base block 12 into a lower port of the flow meter FM, and then through the flow meter along the passageway leg L6. The gas then exits the device GSD1 along an exit passageway leg L7 in the base block 12. Another flow control valve 19a (FIG. 3) fits tightly in, and is sealed, into a bore opening 12d in the top ledge TL. This valve 19a is in communication with the passageway leg L7 and controls the flow of the tested gas from the gas sampling device GSD1. Opening the valve 19a allows gas to exit the gas sampling device GSD1.

Main Flow Path

Passageways, terminal orifices, and openings are formed in the blocks 12, 17, 20 and 21 by machining using conventional equipment, thereby avoiding within the assembly A itself the use of conventional compression fittings normally required by tubing. The main flow path FP depicted by the arrow a in FIG. 3E illustrates how gas flows into and through my sampling device GSD1. The length of the main flow path FP is less than 36 inches, and typically ranges from 6 to 20 inches in one embodiment. The segment or leg L4 of the passageway expands into an enlarged chamber that functions as the light transmission zone LTZ that typically has a cylindrical configuration with a length from 1 to 20 inches and a diameter from 0.5 to 2.0 inches in one embodiment. The other legs of the passageway are typically formed by drilling, and typically have a cylindrical configuration with a diameter from 0.06 to 0.5 inch in one embodiment.

Figures 8A, 8B:
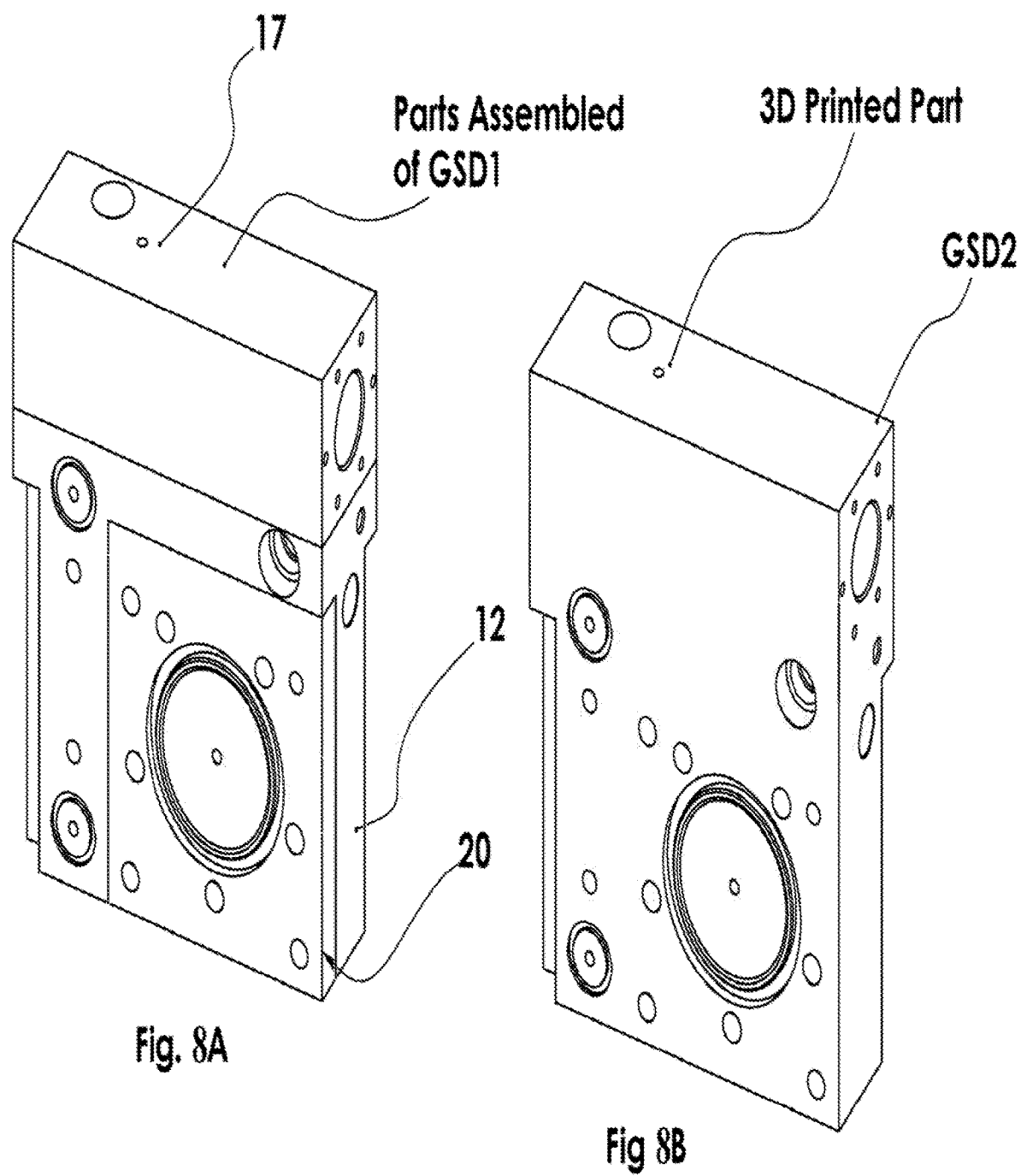
FIGS. 8A and 8B depict a second embodiment comprising a unitary block.

Although this first embodiment of the gas sampling device GSD1 uses several blocks, alternate embodiments using far fewer blocks may be employed such as, for example, the gas sampling device GSD2 illustrated in FIG. 8B, and the gas sampling device GSD3 illustrated FIGS. 9A and 9B.

FIGS. 8A and 8B

FIG. 8A shows an assembly of the base block 12, a cell block 17, an intermediate block 20, and an outer block 21 of the first embodiment GSD1. FIG. 8B shows the same functionality of these four blocks integrated into a single, unitary component that is fabricated with 3D printing or additive manufacturing techniques. All of the internal passageways of the first embodiment GSD1 may be included in a single unit with the 3D printing.

FIGS. 9A and 9B

FIGS. 9A and 9B illustrates how the intermediate block and the base block 12 can be assembled using a single flat gasket as an alternative to the use of separate O-ring seals on each of the connecting passageways as described in the first embodiment GDS1. In a like manner, the O-ring seals between any two blocks, as shown in 20 and 12 could be replaced with a flat gasket 50 as depicted in FIGS. 9A and 9B.

SCOPE OF THE INVENTION

The above presents a description of the best mode I contemplate of carrying out the gas sampling device and method, and of the manner and process of making and using them, in such full, clear, concise, and exact terms as to enable a person skilled in the art to make and use. The gas sampling device and method is, however, susceptible to modifications and alternate constructions from the illustrative embodiments discussed above which are fully equivalent. Consequently, it is not the intention to limit the gas sampling device and method to the particular embodiments disclosed. On the contrary, the intention is to cover all modifications and alternate constructions coming within the spirit and scope of the gas sampling device and method as generally expressed by the following claims, which particularly point out and distinctly claim the subject matter of the invention:

The invention claimed is:

1. A gas sampling device comprising
a liquid separator block, a gas analyzer block, and a metering valve connected together to provide a gas passageway through the blocks and metering valve from an inlet to an outlet along a predetermined flow path through the device,
said gas analyzer block and liquid separator block each having planner faces that are adjacent and in contact with and abutting each other, and
said gas analyzer block and liquid separator block each including a passageway leg of the gas passageway, said passageway legs each respectively terminating in an opening in the exterior faces of said gas analyzer block and liquid separator block,
said flow path proceeding from the inlet through the liquid separator block, and then through the gas analyzer block and out the outlet through sealed connection points along the passageway where faces of the adjacent gas analyzer block and liquid separator block abut and contact each other and the openings in their respective faces are aligned,
thereby eliminating tubing connections between adjacent blocks.

2. The gas sampling device of claim 1 where the flow path has a length that is less than 36 inches.

3. The gas sampling device of claim 2 including a flow meter along the flow path.

4. The gas sampling device of claim 2 where the passageway mainly has a cylindrical configuration with a diameter of less than 0.50 inch.

5. The gas sampling device of claim 2 is compact having a length less than 16 inches, a depth less than 16 inches, and a height less than 16 inches.

* * * * *